United States Patent
Hoeppner (10) Patent No.: US 9,687,287 B2
(45) Date of Patent: Jun. 27, 2017

(54) IMPACT LOAD-LIMITING SURGICAL IMPACTOR

(71) Applicant: Biomet Manufacturing, LLC, Warsaw, IN (US)

(72) Inventor: Jacy Hoeppner, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 385 days.

(21) Appl. No.: 14/309,441

(22) Filed: Jun. 19, 2014

(65) Prior Publication Data

US 2015/0366601 A1    Dec. 24, 2015

(51) Int. Cl.
*A61B 17/92* (2006.01)
*A61F 2/46* (2006.01)
*A61B 17/88* (2006.01)
*A61B 17/90* (2006.01)

(52) U.S. Cl.
CPC .............. *A61B 17/92* (2013.01); *A61B 17/88* (2013.01); *A61B 17/8872* (2013.01); *A61B 17/921* (2013.01); *A61F 2/46* (2013.01); *A61F 2/4603* (2013.01); *A61B 2017/90* (2013.01); *A61B 2017/922* (2013.01); *A61B 2017/924* (2013.01); *A61F 2002/4681* (2013.01)

(58) Field of Classification Search
CPC . A61B 17/88; A61B 17/8872; A61B 2017/90; A61B 17/92; A61B 17/921; A61B 2017/922; A61B 2017/924; A61F 2/46; A61F 2/4603; A61F 2002/4681; B25D 1/02; B25D 1/12; B25G 1/01
See application file for complete search history.

(56) References Cited

U.S. PATENT DOCUMENTS

| | | | |
|---|---|---|---|
| 4,609,054 A | 9/1986 | Nilsson et al. | |
| 5,282,805 A | 2/1994 | Richelsoph et al. | |
| 7,172,598 B2 * | 2/2007 | Ball | A61F 2/4637 606/99 |
| 7,708,739 B2 | 5/2010 | Kilburn et al. | |
| 8,876,837 B2 * | 11/2014 | Smith | A61B 17/56 606/99 |
| 2005/0097708 A1 | 5/2005 | Crawford | |
| 2007/0149981 A1 | 6/2007 | Bhattacharyya | |
| 2009/0222019 A1 | 9/2009 | Bhattacharyya | |
| 2013/0006276 A1 | 1/2013 | Lantz et al. | |
| 2013/0261681 A1 | 10/2013 | Bittenson | |
| 2013/0331849 A1 | 12/2013 | Splieth et al. | |

* cited by examiner

*Primary Examiner* — Larry E Waggle, Jr.
(74) *Attorney, Agent, or Firm* — Schwegman Lundberg & Woessner, P.A.

(57) ABSTRACT

The present invention provides a surgical impactor that includes an impact head, an impacting portion connected to the impact head and a load-transmitting stem connecting the impacting portion to the impact head. The impact head has an impact surface that can be struck by a tool such as a mallet. The load-transmitting stem includes at least one load-limiting resistor. The load-limiting resistor is configured to lock to the impact head and unlock from the impact head when an overload force is applied to the impact surface of the impact head.

18 Claims, 6 Drawing Sheets

IMPACT LOAD-LIMITING SURGICAL IMPACTOR

BACKGROUND OF THE INVENTION

1. Field of the Invention

The present invention relates to impactors, and, more particularly, to surgical impactors.

2. Description of the Related Art

Impactors are often used during surgery to help place and fixate implants within a patient. An impactor allows a surgeon to transfer force from a tool, such as a mallet, to the implant to better seat the implant within the patient. The surgeon must be careful when striking the impactor, as striking the impactor with excessive force can cause damage to the implantation site. The surgeon also does not usually know exactly how much force is being applied to the implant through the impactor, relying on experience to determine whether enough or too much force is being applied.

Load-limiting impactors are known that can limit or control the amount of force being transferred from the impactor to the implant. However, many of these load-limiting impactors are difficult to reset or only last for one excessive force strike.

What is needed in the art is a surgical impactor that can limit the force being applied through the impactor.

SUMMARY OF THE INVENTION

The present invention provides a surgical impactor with a load-limiting resistor that is configured to connect a load-transmitting stem to an impact head until an overload force is applied to the impact head.

The invention in one form is directed to a surgical impactor that includes an impact head, an impacting portion connected to the impact head and a load-transmitting stem connecting the impacting portion to the impact head. The impact head includes an impact surface that can be struck by a tool such as a mallet. The load-transmitting stem includes at least one load-limiting resistor that is configured to lock to the impact head and unlock from the impact head when an overload force is applied to the impact surface.

An advantage of the present invention is that it provides a load-limiting impactor which is easy and quick to reset.

Another advantage is that the impactor can be configured to be reusable.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
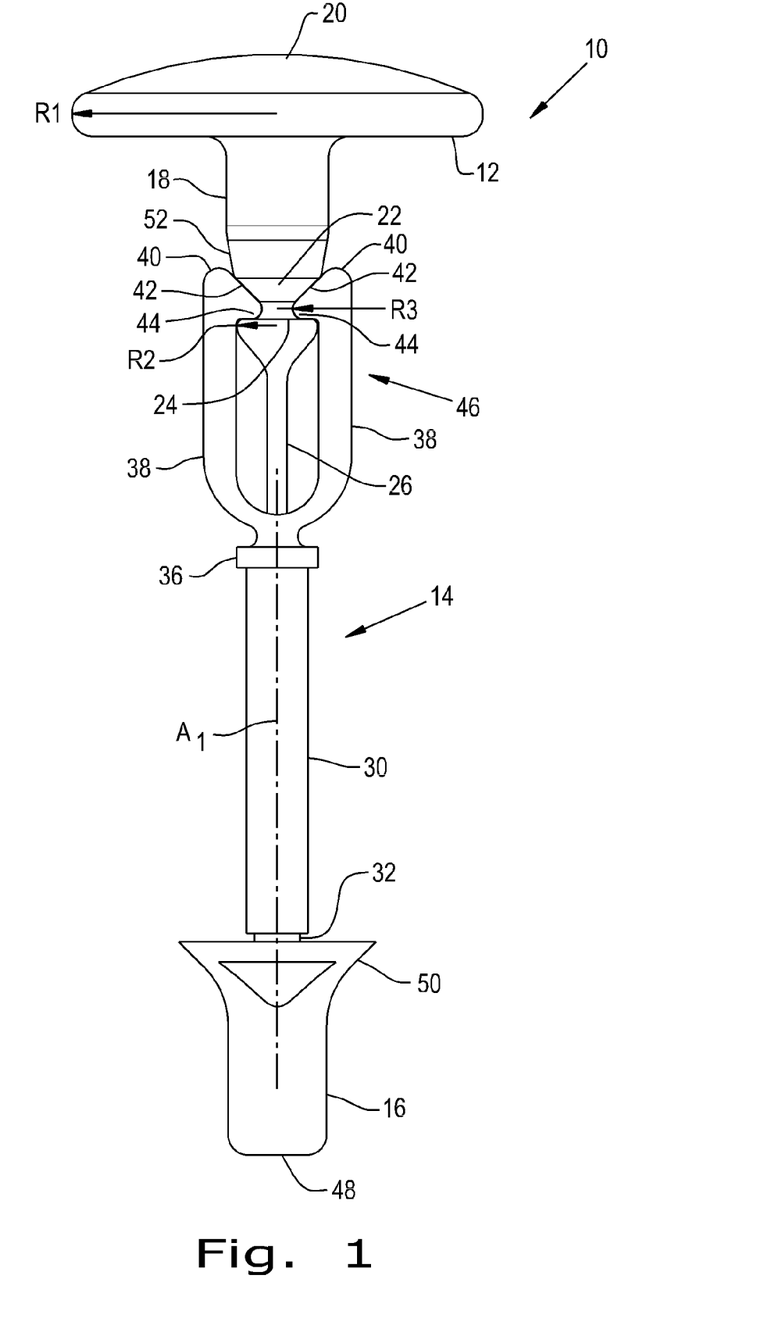
FIG. 1 is a perspective view of an embodiment of the present invention.

Referring now to the drawings, and more particularly to FIG. 1, there is shown a surgical impactor 10 which generally includes an impact head 12, a load-transmitting stem 14 and an impacting portion 16. The impact head 12 includes a base 18 with an impact surface 20 that is designed to be struck by a tool, such as a mallet, to transmit force through the surgical impactor 10 to an implant, securing the implant within a patient. As such, the impact surface 20 can have an impact radius R1 that makes the impact surface 20 an easy target for a user to strike with a mallet. The impact surface 20 shown in FIG. 1 is shaped as a circular disk, but the shape can be varied. The base 18 can be cylindrically shaped and have a groove 22 formed across a circumference of the base 18. The groove 22 can have a major radius R2 and a minor radius R3, forming a ledge 24 in the groove 22 that the load-transmitting stem 14 can lock on to. The impact head 12 can also have an elongate portion 26 on a side of the groove 22 opposite the impact surface 20. The elongate portion 26 can be a generally straight cylindrical portion with a small diameter that is sized to fit within a bore 28 (shown in FIG. 3) formed in the load-transmitting stem 14. The impact head 12 can be made of any suitable material(s) capable of withstanding the striking forces of a mallet, or similar tool, and transmitting the striking forces throughout the impactor 10.

Figure 2:
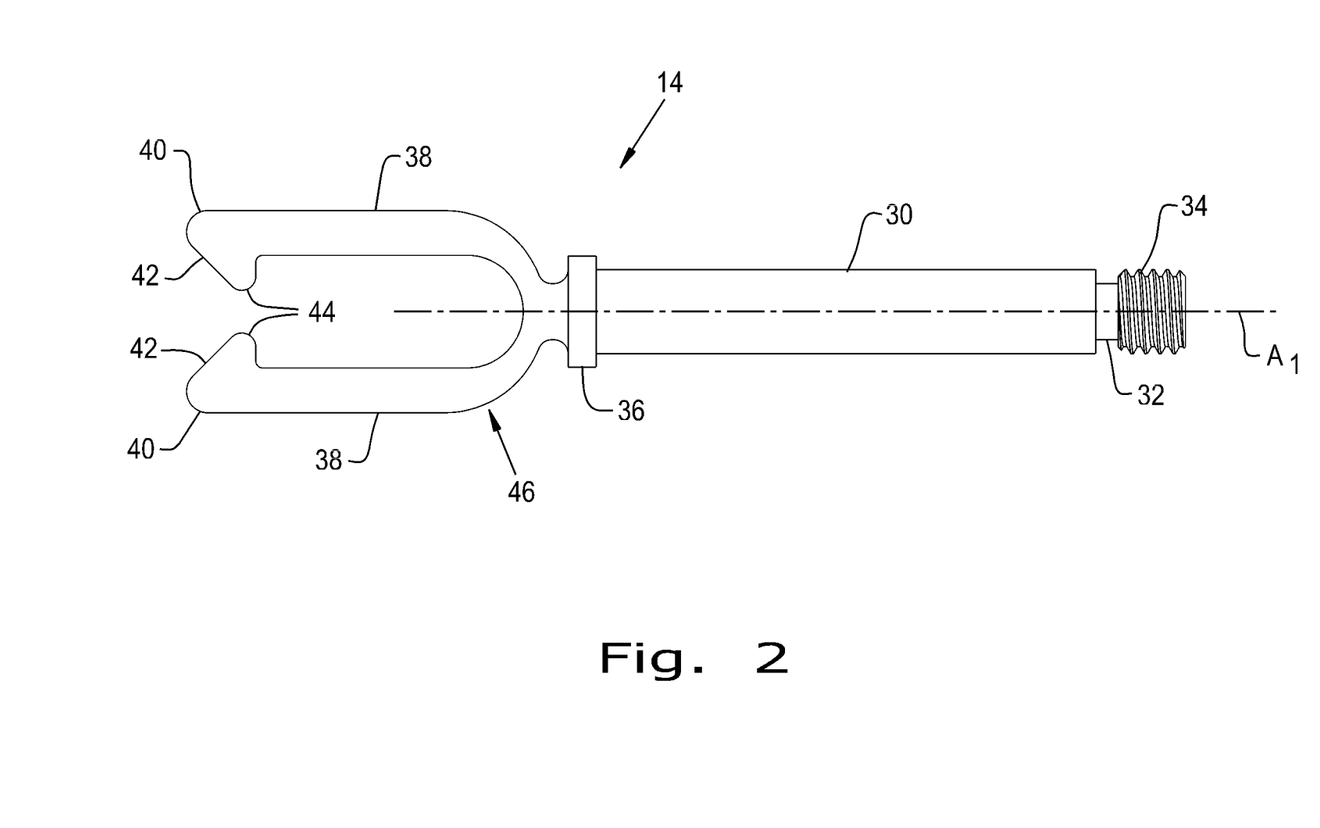
FIG. 2 is a perspective view of a load-transmitting stem of the present invention.
Figure 3:
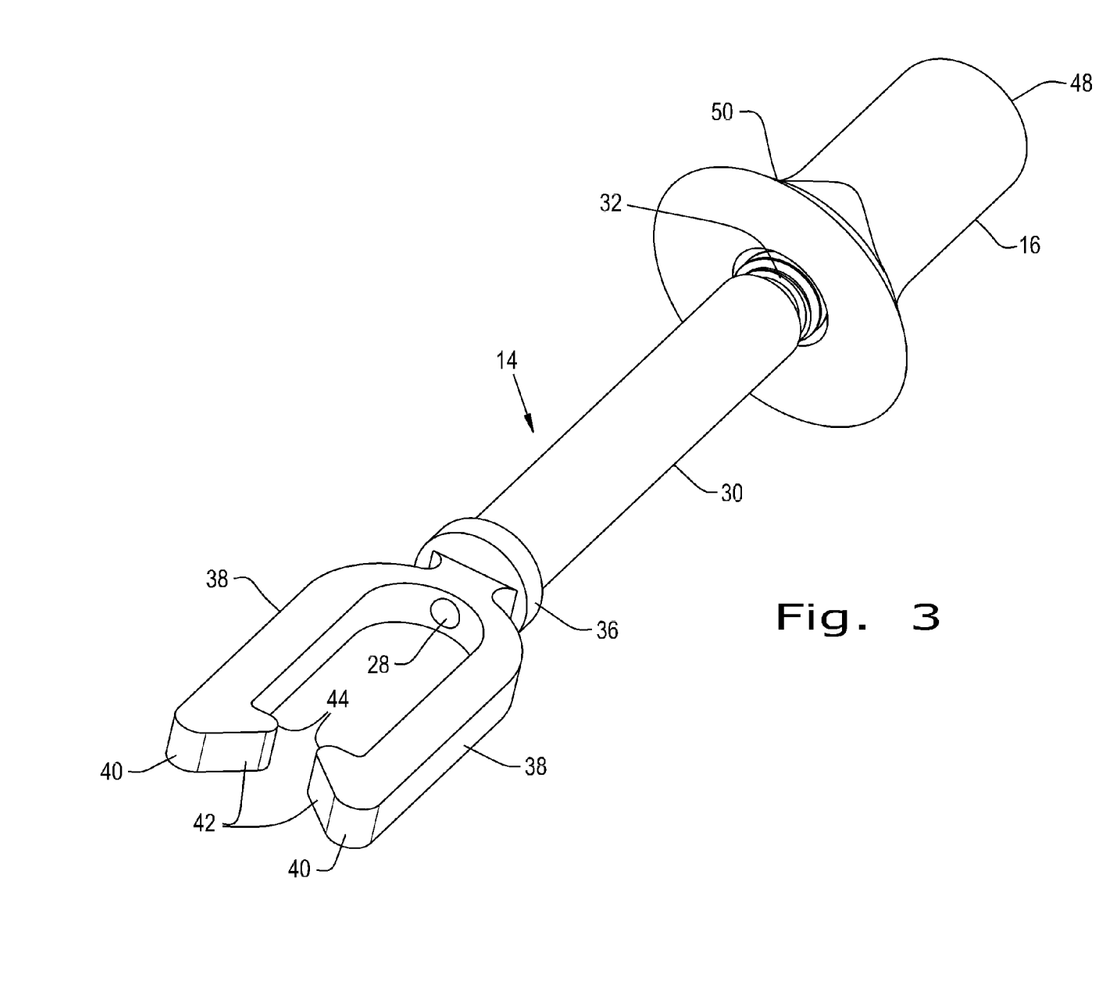
FIG. 3 is a perspective view of a load-transmitting stem and impacting portion of the present invention.

The load-transmitting stem 14, shown unattached to other components of the impactor 10 in FIG. 2, connects the impact head 12 and the impacting portion 16. The load-transmitting stem 14 can include an elongated cylindrical base 30 with a small diameter region 32 that has a threading 34 and a large diameter region 36. The base 30 can define an axis A1 that is the longitudinal axis of the load-transmitting stem 14 at the center of base 30. At least one load-limiting resistor 38 is attached to the base 30 and is shown throughout FIGS. 1-5 as a load-limiting clip 38. While the load-limiting resistor 38 is shown as a load-limiting clip in FIGS. 1-5, other resistors could be used including spring-loaded mechanisms, such as a ball plunger, or differently shaped material projections that can press into the groove 22. Further guidance on configuring an appropriate load-limiting resistor 38 will be described below, but for ease of description the load-limiting resistor 38 will be referred to as a load-limiting clip. The load-limiting clip 38 has an arcuate shape and can include a hooked end 40. The hooked end 40 can partly rest in the groove 22 when the load-transmitting stem 14 is locked to the impact head 12, providing frictional and pressing forces to keep the load-transmitting stem 14 locked to the impact head 12. The hooked end 40 has a hook surface 42, angled relative to the axis A1, that is partly in contact with the major radius R2 when the load-transmitting stem 14 is locked to the impact head 12 and a hook tip 44 that presses into the groove 22 orthogonally to the axis A1. As shown in FIGS. 1-3, the load-transmitting stem 14 can include two load-limiting clips 38 that are mirrors of each other, forming a wish bone shaped load limiter 46 with hooked ends 40. In such a configuration, both clips 38 will lock to the groove 22 simultaneously. The base 30 can be made from any material capable of withstanding the impact forces that will be transmitted through the impactor 10. The clip(s) 38 can be made from an elastically deformable material that is capable of withstanding repeated stretching without failure, such as Nitinol. It is useful for the clip(s) 38 to have a resting state that is biased toward the axis A1 when a force is not applied to the clip(s) 38. This biases the hook tip(s) 44 toward the impact head 12 when the impactor 10 is assembled, increasing the holding force that the clip(s) 38 exert on the impact head 12. The load-transmitting stem 14 is locked to the impact head 12 by the clip(s) 38 pressing into the groove 22 as well as the elongate portion 26 of the impact head 12 being placed partially within the bore 28 of the load-transmitting stem 14.

The impacting portion 16 is connected to the load-transmitting stem 14 at an end opposite the impact head 12. The impacting portion 16 can have a threaded opening (not shown) that corresponds to the threading 34 of the load-transmitting stem 14, allowing for various designs of impacting portions 16 to be attached to the load-transmitting stem 14. The impacting portion 16 may take any shape that gives desired force transmission from the impact surface 20 to an implant. It is useful for the impacting portion 16 to have an impacting surface area 48, which will contact the implant during use, with a lower surface area than the impact surface 20. Such a configuration allows for a greater pressure to be exerted at the impacting surface area 48 than is applied to the impact surface 20. The impacting surface area 48 can be flat or angled to a smaller area if greater pressure magnification is desired. The impacting portion 16 can also have a taper 50 formed thereon to provide a gripping surface for a user to hold during use, if desired. The impacting portion 16 can be made of any suitable biocompatible material that is capable of withstanding the forces being transmitted to an implant without failure.

Figure 4:
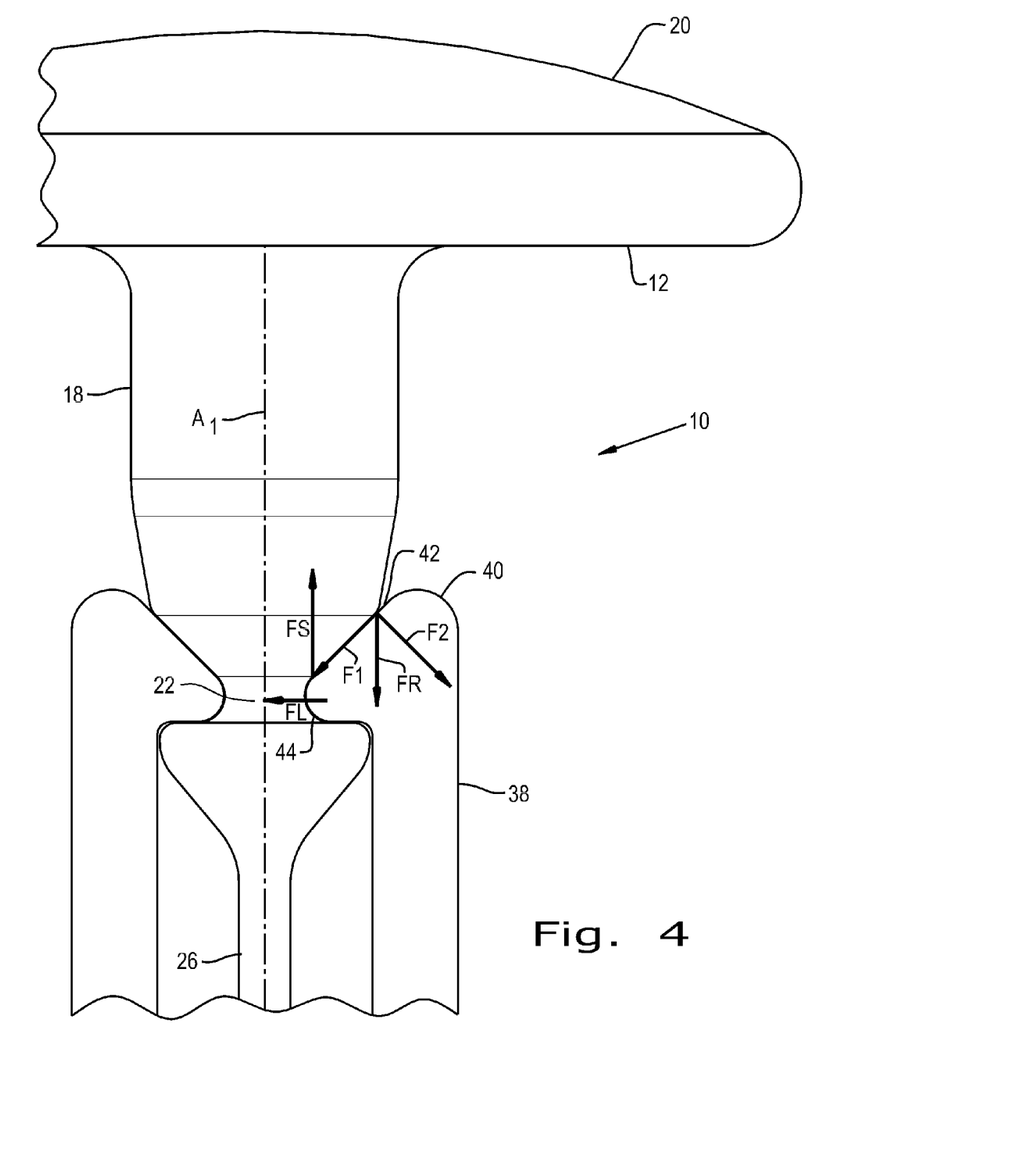
FIG. 4 is a sectional view of an embodiment of the present invention.

To use the impactor 10 of the present invention, the impacting surface area 48 is pressed against an implant or area in a patient's body that a user wishes to apply pressure against. Once the impacting surface area 48 is pressed against the desired target, the user strikes the impact surface 20 with a tool, such as a mallet, to produce a striking force which transmits through the impact head 12 to the load-limiting clip(s) 38, through the load-transmitting stem 14 to the impacting portion 16 and through the impacting portion 16 to the impacting surface area 48. As can be seen in FIG. 4, when a resultant force FR directed along axis A1 (such as the striking force or weight of the impact head 12) is applied to the hook surface 42, a surface force F1 is produced along the hook surface 42 and an outward force F2 is produced orthogonally to the surface force F1. The resultant force FR is therefore a sum of the magnitude and direction of surface force F1 and outward force F2. The surface force F1 will bias the load-limiting clip(s) 38 toward the impact head 12 while the outward force F2 will bias the clip(s) 38 away from the impact head 12 during use. The load-limiting clip(s) 38 can naturally produce a locking force FL that is directed toward the groove 22. To simplify the example, the locking force FL is shown as purely horizontal (orthogonal) to the axis A1, but in actual practice is more likely to have both a horizontal and a vertical component. The horizontal force components of the locking force FL and surface force F1 press against the groove 22, forming a static frictional force FS. When the clip(s) 38 is locked to the groove 22, the sum of the horizontal components of the locking force FL and surface force F1 will be equal to or greater than the horizontal component of the outward force F2, and the static frictional force FS will be equal to or greater than the resultant force FR along the axis A1.

The hook surface 42 is angled such that when an overload force is applied to the impact surface 20 (which transmits to the hook surface 42), the horizontal component of the outward force F2 will be greater than the sum of the horizontal components of the surface force F1 and locking force FL, causing a net force in the horizontal direction against the load-limiting clip(s) 38 away from the axis A1. The net force in the horizontal direction can cause the load-limiting clip(s) 38 to move relative to the groove 22 and unlock from the groove 22. When the clip(s) 38 unlocks from the groove 22, the resultant force FR in the downward direction of the axis A1 that is greater than the static frictional force FS will cause the elongate portion 26 to travel down the bore 28, be counteracted by dynamic frictional force created along the hook surface 42 and/or cause the outward force F2 to have a horizontal component sufficient to deform the load-limiting clip(s) 38 orthogonally away from the axis A1. If the load-limiting clip(s) 38 deform orthogonally away from the axis A1, the angle of direction relative to the axis A1 at which the surface force F1 and outward force F2 extend can change. This change can reduce the proportion of the resultant force FR that will be directed downward along the axis A1 through the load-limiting clip(s) 38 and transmitted through the load-transmitting stem 14 to the impacting portion 16. When the load-limiting clip(s) 38 unlocks from the groove 22, the impact head 12 will also tend to slip relative to the load-limiting clip(s) 38 which reduces the force that the load-transmitting stem 14 is able to transmit to the impacting portion 16.

If the excess force is great enough to cause the bottom of the impact surface 20 to come into contact with the clip(s) 38, or other rigid parts of the load-transmitting stem 14, any force over the amount necessary to cause that event will be transmitted to the impacting surface area 46. To counteract such an event from happening, it can be useful to include a friction region 52 on the impact head 12 between the groove 22 and the impact surface 20. The friction region 52 can be a roughened area or a different material that forms a high dynamic coefficient of friction with the hook tip 44 and hook surface 42, helping to dissipate any excess downward forces and prevent the excess force from being transmitted to the impacting surface area 46. The clip(s) 38 can also be configured to deform until breaking when the overload force is applied, with some or all of the excess force being absorbed by the clip(s) 38 when it deforms and breaks. If such a configuration is chosen, it is useful for the clip(s) 38 to attach to the base 30 in a reversible manner for easy replacement.

Once the clip(s) 38 unlock from the groove 22 and the load-transmitting stem 14 is no longer attached to the impact head 12, the impactor 10 can be reset to transmit limited forces by placing the clip(s) 38 back into the groove 22, re-locking the load-transmitting stem 14 to the impact head 12. If the clip(s) 38 is configured to break when an overload force strikes the impact surface 20, the clip(s) 38 should be replaced before re-locking to the groove 22. The clip(s) 38 can also be replaced before resetting the impactor 10 if the excess force has irreversibly deformed the clip(s) 38 too much to re-lock with the groove 22 or if friction during movement of the clip(s) 38 wears away the hook tip 44 and/or hook surface 42 to render the clip(s) 38 less effective.

Figure 5:
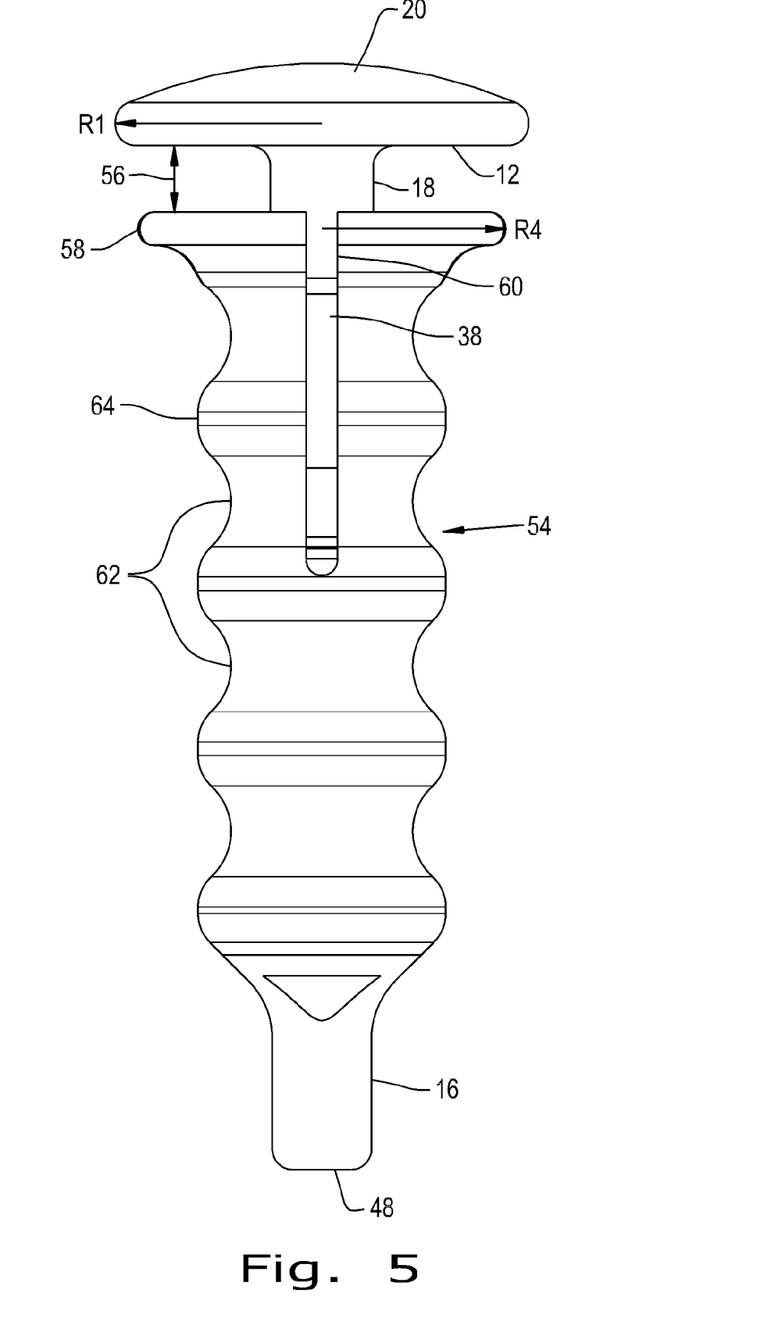
FIG. 5 is a perspective view of another embodiment of the present invention.

Referring now to FIG. 5, the impactor 10 can include a handle 54 covering the impactor 10 between the impact surface 20 and the impacting portion 16 with a handle gap 56 between the impact surface 20 and an upper end 58 of the handle 54. The handle 54 can have one or more openings 60 that fit over the load-limiting clip(s) 38 and allow the load-limiting clip(s) 38 to move through the opening(s) 60 in the event that an overload force pushes the impact head 12 down so much that the load-limiting clip(s) 38 are pushed outwardly away from the axis A1. The upper end 58 can have a handle radius R4 that is substantially the same as impact radius R1, as well as multiple handle grooves 62 to provide a gripping surface 64 for the user to hold while using the impactor 10. The handle 54 can also be configured to "slip" in the event an overload force is applied to the impact surface 20, so some of the excess force goes toward overcoming frictional forces to move the handle 54 down the impactor 10 along axis A1 in the event that the impact surface 20 is pushed into the upper end 58 of the handle 54. The handle 54 can be formed of any suitable material for being placed over components of the impactor 10, with polymers being an especially useful material.

Figure 6:
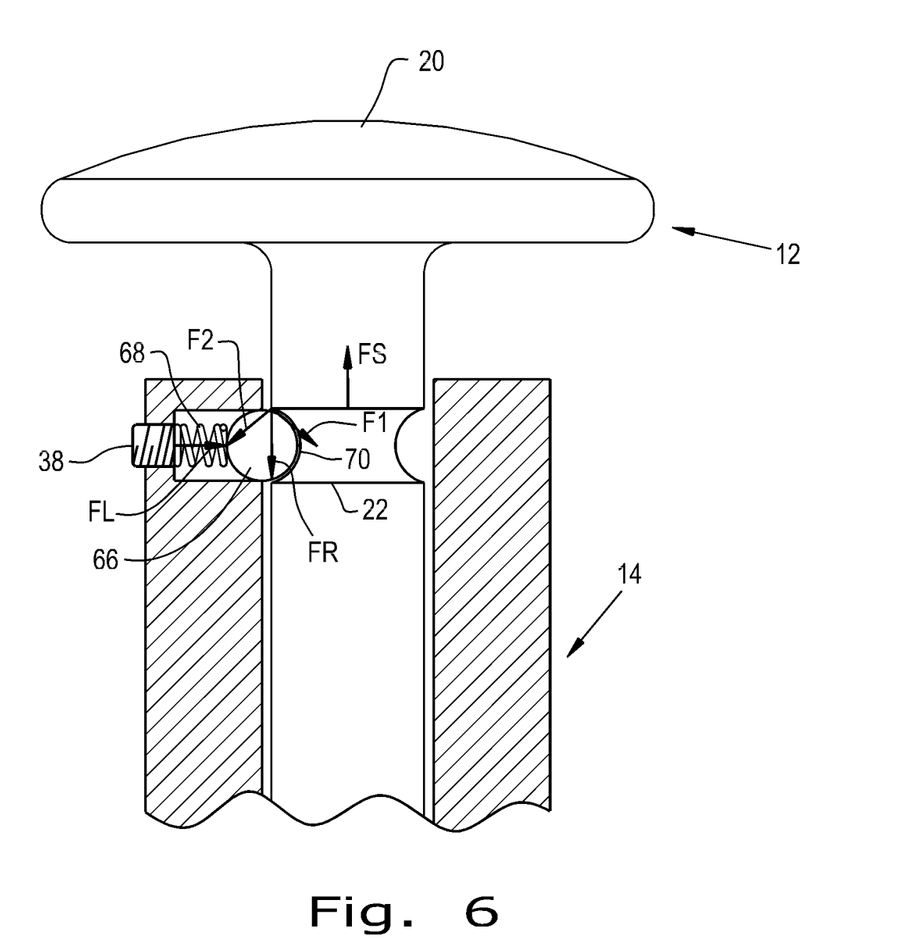
FIG. 6 is a perspective view of yet another embodiment of the present invention.

As previously described, different load-limiting resistors 38 can be used other than a load-limiting clip. The main design concerns are how much force is desired to be resisted by the load-limiting resistor 38 before unlocking the load-transmitting stem 14 from the impact head 12 and how the geometry of the load-limiting resistor 38 converts impact force applied to the impact surface 20 into outward force F2 that works to unlock the load-transmitting stem 14 from the impact head 12. For example, a ball plunger could be used as the load-limiting resistor 38 in place of a clip, as shown in FIG. 6. The ball plunger 38 can have a spherical ball 66 that is pressed into the groove 22 by a spring 68 connected to the base 30. The ball 66 contacts the groove 22 along a curved surface 70, which will re-direct downward force applied to the impact surface 20 into outward force F2, similarly to the hook surface 42 previously described. A locking force FL still produces a frictional force FS, but is provided by the spring 68 pressing the ball 66 into the groove 22. In this sense, the locking force FL that opposes the horizontal component of the outward force F2 will, for a spring that follows Hooke's Law, be determined by $F=kx$, where k is the spring constant of spring 68 and x is the horizontal compression of the spring 68 relative to its resting state. The spring constant k therefore takes the place of the natural resistance to deformation that the clips' material had to oppose the outward force F2, and the horizontal component of the outward force F2 needed to unlock the load-limiting resistor 38 from the impact head 12 would be equivalent to the spring constant k multiplied by the horizontal distance x required to take the load-limiting resistor 38 out of contact with the groove 22, which in the case of a ball plunger would be the radius of the curved surface 70. Other shapes besides a ball could also be pressed into the groove 22 by a spring 68 or a different pressing force to give different re-direction(s) of downward force applied to the impact surface 20. It is therefore contemplated that different mechanisms, shapes and materials can be employed in the load-limiting resistor(s) 38 of the present invention.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical impactor, comprising:
   an impact head having an impact surface;
   an impacting portion connected to said impact head; and
   a load-transmitting stem connecting said impacting portion to said impact head, said load-transmitting stem defining a stem axis and including at least one load-limiting resistor configured to lock to said impact head and unlock from said impact head when an overload force is applied to said impact surface;
   wherein said load-transmitting stem includes a bore formed in a direction of said stem axis and said impact head includes an elongated portion, said bore being configured to allow movement of said elongated portion through said load-transmitting stem when said overload force is applied to said impact surface.

2. The surgical impactor according to claim 1, wherein said impact head has a groove formed therein that said at least one load-limiting resistor locks to.

3. The surgical impactor according to claim 2, wherein said impact head includes a friction region between said groove and said impact surface.

4. The surgical impactor according to claim 3, wherein said at least one load-limiting resistor is configured to press into said friction region when said overload force is applied to said impact surface.

5. The surgical impactor according to claim 2, wherein said at least one load-limiting resistor is at least one of a load-limiting clip and a ball plunger.

6. The surgical impactor according to claim 5, wherein said ball plunger includes a spherical ball including a curved surface shaped to press into said groove and a spring pressing said ball into said groove.

7. The surgical impactor according to claim 5, wherein said load-limiting clip includes a hooked end with a hook tip.

8. The surgical impactor according to claim 7, wherein said load-limiting clip includes a hook surface in contact with said groove.

9. The surgical impactor according to claim 5, wherein said load-transmitting stem includes two load-limiting resistors.

10. The surgical impactor according to claim 9, wherein said two load-limiting resistors are configured to simultaneously lock to said groove and simultaneously unlock from said groove when said overload force is applied to said impact surface.

11. The surgical impactor according to claim 10, wherein said two load-limiting resistors together form a wishbone shaped load limiter.

12. The surgical impactor according to claim 1, wherein said at least one load-limiting resistor is configured to produce an outward horizontal force that is orthogonal to said stem axis when said overload force is applied to said impact surface.

13. The surgical impactor according to claim 1, further including a handle at least partially covering said load-transmitting stem.

14. The surgical impactor according to claim 13, wherein said handle includes an opening configured to allow said at least one load-limiting resistor to pass through when said overload force is applied to said impact surface.

15. The surgical impactor according to claim 13, wherein said handle includes a first portion defining a first handle radius and a second portion having a plurality of handle grooves formed therein, said first handle radius being substantially the same as an impact radius defined by said impact surface.

16. The surgical impactor according to claim 1, wherein said impacting portion has a cylindrical shape.

17. The surgical impactor according to claim 16, wherein said impact surface defines an impact radius and said impacting portion defines an impactor radius, said impact radius being greater than said impactor radius.

18. A method of transmitting force in a surgical procedure, comprising the steps of:
providing a surgical impactor including an impact head with an impact surface and an elongated portion, an impacting portion connected to said impact head and a load-transmitting stem connecting said impact head to said impact surface, said load-transmitting stem being connected to said impact head by at least one load-limiting resistor, said load-transmitting stem defining a stem axis and including a bore formed in a direction of said stem axis;
placing said impacting portion against a surgical surface; and
striking said impact surface, wherein striking said impact surface with an overload force will cause said at least one load-limiting resistor to disconnect from said impact head allowing movement of said elongated portion through said load-transmitting stem.

\* \* \* \* \*